United States Patent [19]

Cobb

[11] 4,125,536
[45] Nov. 14, 1978

[54] PYROLYSIS PRODUCT OF N-SUBSTITUTED-1-CYCLOHEXENE-1,2-DICARBOXIMIDES

[75] Inventor: Raymond L. Cobb, Bartlesville, Okla.

[73] Assignee: Phillips Petroleum Company, Bartlesville, Okla.

[21] Appl. No.: 802,168

[22] Filed: May 31, 1977

Related U.S. Application Data

[62] Division of Ser. No. 603,221, Aug. 8, 1975, Pat. No. 4,056,542, which is a division of Ser. No. 360,962, May 16, 1973, Pat. No. 3,932,457.

[51] Int. Cl.$^2$ .................. C07D 487/10; C07D 487/04
[52] U.S. Cl. .................. 260/326 C; 260/326 N; 260/326.5 F; 260/346.3
[58] Field of Search ..................... 260/326 C

[56] References Cited

U.S. PATENT DOCUMENTS

| | | | |
|---|---|---|---|
| 2,551,573 | 5/1951 | Downing | 260/653.3 |
| 2,781,359 | 2/1957 | Heckert et al. | 260/326 C |
| 3,078,228 | 2/1963 | Smith et al. | 260/326 C |
| 3,236,903 | 2/1966 | Milton | 260/666 R |
| 3,291,801 | 12/1966 | Montgomery | 260/289 |
| 3,932,457 | 1/1976 | Cobb | 260/326 N |

OTHER PUBLICATIONS

Gryaznov et al., Chem. Abs. 56, 10973i (1962).
Tsuji et al., Chem. Abs. 72, 66629e (1970).
Salakhov et al., Chem. Abs. 76, 59034m.
Zahovszky et al., Chem. Abs. 80, 95185c (1973).
Lawton et al., J. Organic Chem. 24, pp. 26–28 (1954).

*Primary Examiner*—Paul M. Coughlan, Jr.
*Assistant Examiner*—Mark L. Berch

[57] ABSTRACT

Pyrolysis of N-substituted-1-cyclohexene-1,2-dicarboximide gives N,N'-substituted-pyromellitdiimides. Pyrolysis of N-substituted-1-cyclohexene-1,2-dicarboximide in the presence of N-substituted maleimides produces N,N'-substituted-3,4,5,6-tetrahydropyromellitdiimide and the Diels-Alder dimer of N-substituted-1,3-butadiene-2,3-dicarboximide.

3 Claims, No Drawings

PYROLYSIS PRODUCT OF N-SUBSTITUTED-1-CYCLOHEXENE-1,2-DICARBOXIMIDES

This is a Divisional application of Ser. No. 603,221, filed August 8, 1975 now U.S. Pat. No. 4,056,542, patented Nov. 1, 1977; which is a Divisional application of Ser. No. 360,962, filed May 16, 1973, now U.S. Pat. No. 3,932,457, patented Jan. 13, 1976.

FIELD OF THE INVENTION

The invention relates to the production of pyromellitdiimides. In another aspect, the invention relates to tetrahydropyromellitdiimides and methods to produce same. In a further aspect, the invention relates to the dimer of N-substituted-1,3-butadiene-2,3-dicarboximide and methods to produce same.

BACKGROUND OF THE INVENTION

In the field of polymer chemistry, the search continues for new compounds suitable as monomers for the preparation of polymers useful for a variety of purposes. New routes to known monomers also are valuable in providing alternative methods of producing valuable monomers, such as pyromellitic anhydride which is particularly useful in producing thermally stable heterocyclic polymers such as described in 16 *Encycl. Chem. Tech.*, 42 (1968).

OBJECTS OF THE INVENTION

It is an object of the invention to provide new compositions of matter useful as monomers in the formation of polymeric products.

Another object of the invention is the provision for new routes to useful monomers.

Other aspects, objects, and advantages of the present invention will become apparent from a study of the dislcosure, and the appended claims.

DESCRIPTION OF THE INVENTION

I have discovered that the pyrolysis of N-substituted-1-cyclohexene-1,2-dicarboximide (A) results in N,N'-substituted-pyromellitdiimide (B) and the dimer of N-substituted-1-3,-butadiene-2,3-dicarboximide (C). The N,N'-substituted-pyromellitdiimide (B) can be hydrolyzed, if desired, to pyromellitic anhydride which is particularly useful in making thermally stable heterocyclic polymers.

I have further discovered that the pyrolysis of N-substituted-1-cyclohexene-1,2-dicarboximide (A) in the presence of N-substituted maleimide (D) yields the Diels-Alder dimer of N-substituted-1,3-butadiene-2,3-dicarboximide (C) and N,N'-substituted-3,4,5,6-tetrahydropyromellitdiimide (E). The material (E) can be readily dehydrogenated to yield the aforesaid N,N'-substituted-pyromellitdiimide (B) which latter, if desired, can be subjected to the aforesaid hydrolysis to the corresponding pyromellitic anhydride. Or, the N,N'-substituted-3,4,5,6-tetrahydropyromellitdiimide (E) can be reacted with an alpha,omega-diamine to produce spongy, rubbery, solids. The Diels-Alder dimer of N-substituted-1,3-butadiene-2,3-dicarboximide (C) can also be reacted with alpha,omega-hydrocarbon diamines to produce polymeric products suitable for a variety of applications, such as drying oils or corrosion inhibitors.

While I do not wish to be bound by theoretical considerations of how these products are produced or in just what fashion the initial reactants form my novel N,N'-substituted-3,4,5,6-tetrahydropyromellitdiimide (E) and Diels-Alder dimer of N-substituted-1,3,-butadiene-2,3-dicarboximide (C), nevertheless, the following representations may assist in understanding the novel reactions and the products I have discovered:

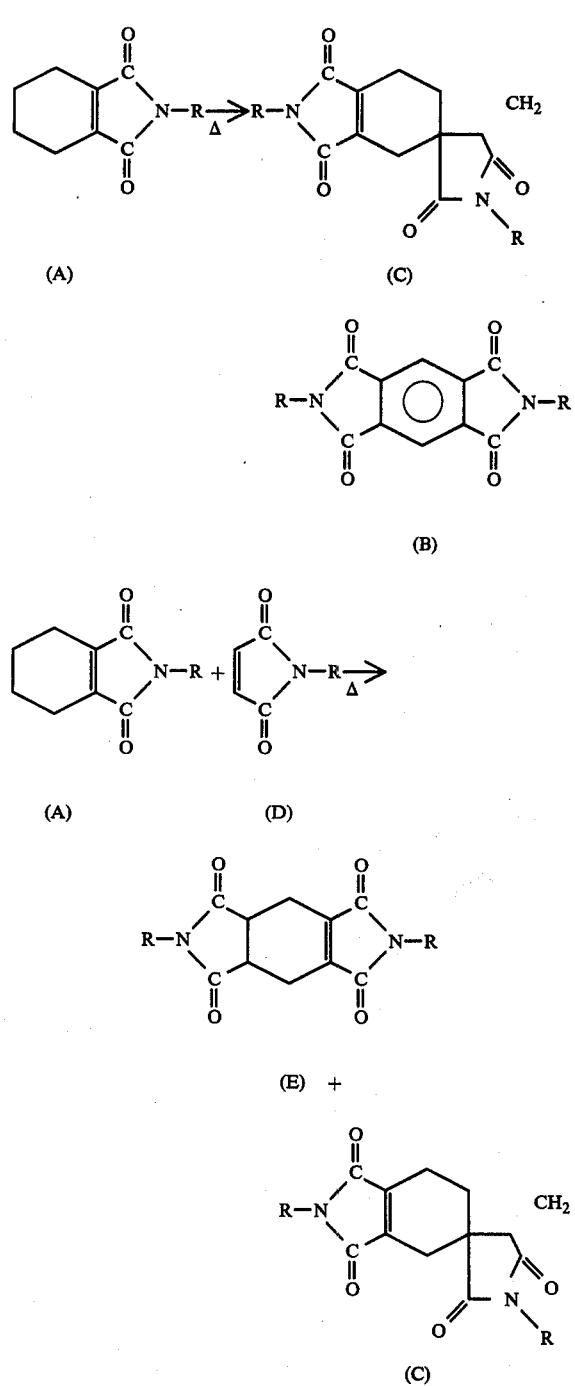

The compounds (C) and (E) may arise, respectively, by the reaction of N-substituted-1,3-butadiene-2,3-dicarboximide (F) with itself or with N-substituted maleimide (D). The formation of the novel compounds (C) and (E) may be visualized as follows:

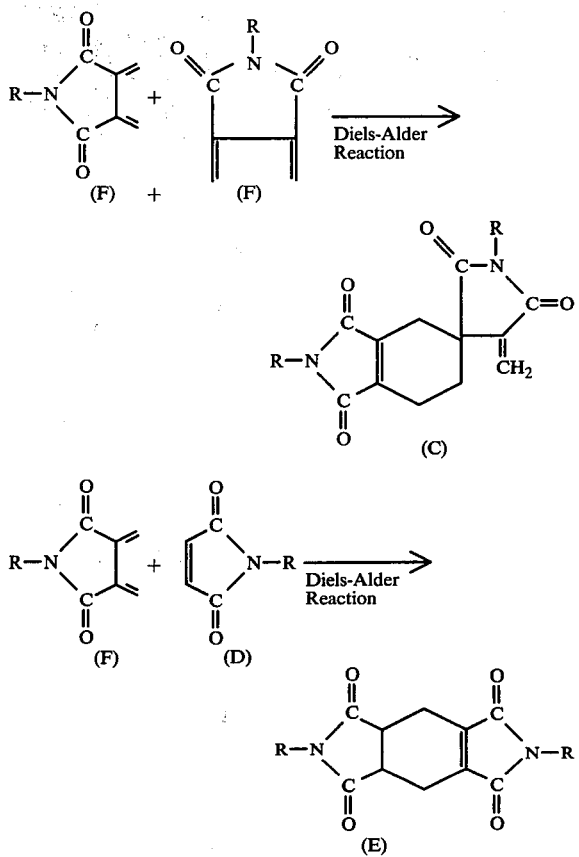

The postulated reactive intermediate N-substituted-1,3,-butadiene-2,3-dicarboximide (F) could be generated from (A) as shown below:

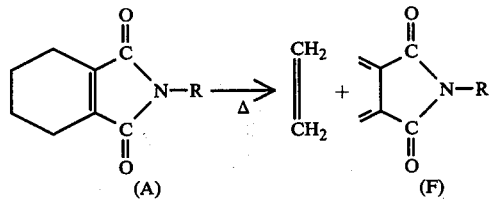

In the above formulae, R can be phenyl or primary alkyl radical, preferably of 1 to 6 carbon atoms. While, in general, the R groups in (A) and (D) are the same, this is not necessary to the reaction, such that where more than one R group appears in a particular compound, or in differing reactants, the R groups can be but are not necessarily the same.

REACTION CONDITIONS

In accordance with my invention, the pyrolysis conversion reaction which I have discovered is conducted under conditions of temperature and pressure sufficient to effectuate the pyrolysis conversion. The reaction can be conducted at suitable elevated temperature and low pressures sufficient to effect the reaction desired. Contact times normally are relatively short, to avoid undue loss or decomposition of reactants, intermediates, and end products. Presently preferred are reaction temperatures in the range of about 500° to 1000° C., presently more preferred in the range of about 700° C. to 800° C. Contacting pressures preferably should be relatively low, such as 0.001 to about 100 mm mercury absolute, presently preferred about 1 to 50 mm mercury absolute. Contact times preferably are short, such as in the range of about 0.001 to 1 second, preferably about 0.005 to 0.1 seconds, though some variance can be practiced.

In effecting the pyrolysis reaction, treating the reactants in the molten condition at the specified temperatures and pressures for very short contacting times is one suitable mode. Treatment can be in a reactor of quartz, or ceramic lined metal reactors such as a ceramic lined titanium autoclave and the effluent from the reactor preferably is collected in a trap at dry ice temperatures, and can be purified such as by recrystallization or preparative gas chromatographic techniques.

While contacting can be and preferably is in the absence of a solvent, solvents are employable where desired or convenient to assist in handling of some of the reactants, and solvents such as the alkyl aryl carboxylates such as methyl benzoate, or various pyridine compounds, or dialkylphthalates, such as dimethyl phthalate, aryl ethers such as diphenyl ether, or other compounds such as benzonitrile, which are relatively inert under the reaction conditions described, can be employed in the process.

EXAMPLES

The examples provided are intended to assist and further illustrate the scope of my invention, and to assist in the understanding thereof. Specific reactions, specific reaction conditions, methods of handling reactions, all should be considered as illustrative and not as limitative of the reasonable scope of my invention as disclosed in this specification including claims.

EXAMPLE I

A charge of 5 g (0.045 mole) N-methylmaleimide and 5 g (0.03 mole) N-methyl-1-cyclohexene-1,2-dicarboximide in 25 g dimethyl phthalate as solvent was passed through a tubular reactor bed of quartz chips at 750° C. and 2.5 mm Hg over a period of 43 minutes using a 50 cc/min purge of $N_2$ to facilitate the passage of the reactants through the reaction zone. The reactor effluent collected in cold traps amounted to approximately 31.5 g. The reactor effluent collected was poured slowly into 600 ml ether with swirling and a precipitate formed. This precipitate was removed by filtration and recrystallized twice from tetrahydrofuran. The solid product (m.p. 200°–203° C.) was shown to be N,N'-dimethyl-3,4,5,6-tetrahydropyromellitdiimide by elemental and mass spectral analyses. Elemental analysis calculated for $C_{12}H_{12}N_2O_4$: % C, 58.09; % H, 4.90; % N, 12.05; Found: % C 58.08; % H, 4.90; % N, 12.05. The molecular weight by mass spectral analysis was found to be 248 (calculated mol. wt. 248) and the mass cracking pattern indicated the product to be N,N'-dimethyl-3,4,5,6-tetrahydropyromellitdiimide.

EXAMPLE II

A charge of 10 g (0.09 mole) N-methylmaleimide and 2.5 g (0.015 mole) N-methyl-1-cyclohexene-1,2-dicarboximide in 7.5 g pyridine reaction diluent containing 0.1 g dimethyl phthalate (glc internal standard) was passed through a tubular reactor bed of quartz chips at 750° C. and 10 mm Hg over a period of 19 minutes using a nitrogen purge. The reactor effluent collected in cold traps amounted to approximately 17.2 g. A glc analysis of the reactor effluent showed the presence of N,N'-dimethyl-3,4,5,6-tetrahydropyromellitdiimide and the dimer of N-methyl-1,3-2,3-dicarboximide. The glc analysis showed 49.8 area % of N,N'-dimethyl-3,4,5,6-tetrahydropyromellitdiimide and 43.8 area % of the dimer of N-methyl-1,3-butadiene-2,3-dicarboximide. Retention times were utilized to verify the presence of N,N'-dimethyl-3,4,5,6-tetrahydropyromellitdiimide and the dimer of N-methyl-1,3-butadiene-2,3-dicarboximide. The sample of N,N'-dimethyl-3,4,5,6-tetrahydropyromellitdiimide used for this purpose was prepared in Example I. The sample of the dimer of N-methyl-1,3-butadiene-2,3-dicarboximide used for this purpose had a melting point of 139°–140° C. and its structure was verified by elemental, mass spectral and nuclear magnetic resonance analyses:

a. Elemental analysis for the dimer of N-methyl-1,3-butadiene-2,3-dicarboximide $C_{14}H_{14}N_2O_4$: Calc'd % C, 61.3; % H, 5.1; % N, 10.2; Found: % C, 61.46; % H, 5.27; % N, 10.93 b. Mass Spectral Analysis for the dimer of N-methyl-1,3-butadiene-2,3-dicarboximide: Mol. wt. 274 (Calc'd 274)

c. $^{13}C$ Nuclear Magnetic Resonance data supported the structure of the dimer of N-methyl-1,3-butadiene-2,3-dicarboximide as shown above by exhibiting resonances specifically from:

3 methylene units
1 quaternary carbon
3 olefinic carbons with no protons attached
1 olefinic carbon with two protons attached
2 methyl groups
3 types of carbonyl groups

EXAMPLE III

A 9.8 g (0.06 mole) molten sample of N-methyl-1-cyclohexene-1,2-dicarboximide was passed through a tubular reactor bed of quartz chips at 700° C. and about 20 mm Hg over a period of ten minutes using a nitrogen purge. The reactor effluent was collected in a mixture of methanol/tetrahydrofuran and stored at dry ice temperature. The precipitate which formed was removed by filtration and recrystallized three times from tetrahydrofuran to give a solid which melted at 375°–378° C. in a sealed tube. The solid sublimed at 350°–360° C. in an open tube. This product was shown to be N,N'-dimethylpyromellitdiimide by elemental, infrared and mass spectral analyses.

EXAMPLE IV

A 0.49 g (0.002 mole) sample of N,N'-dimethyl-3,4,5,6-tetrahydropyromellitdiimide was mixed with 0.29 g (0.002 mole) 1,8-octanediamine and the mixture heated to and maintained at 195° C. for three hours. During the reaction period the mixture became blue-green in color and a gas was evolved. The mixture became viscous and by the end of the reaction period a spongy rubbery polymeric product was formed which was insoluble in tetrahydrofuran.

EXAMPLE V

A 1.61 g (0.0059 mole) sample of the dimer of N-methyl-1,3-butadiene-2,3-dicarboximide was mixed with 0.85 g (0.0059 mole) 1,8-octanediamine and the mixture heated to and maintained at 195° C. for three hours. During the reaction period, a blue-green color developed and a gas was evolved. The viscous liquid product was completely soluble in tetrahydrofuran.

The N,N'-substituted-3,4,5,6-tetrahydropyromellitdiimide compounds of my discovery can be reacted as demonstrated with α,ω-diamines to produce spongy rubbery solids which can be employed for tire cords or molding resins. These N,N'-substituted-3,4,5,6-tetrahydropyromellitdiimides can be readily dehydrogenated in the presence of metals such as palladium, platinum, ruthenium and the like, or by thermal treatment with sulfur to produce the corresponding N,N'-substituted-pyromellitdiimides. As described in 72 *Chem. Abstr.* 66629e (1970), the latter compounds can be readily separated and converted, by hydrolysis, to pyromellitic anhydride. Pyromellitic anhydride is known for making thermally stable heterocyclic polymers such as described in 16 *Encycl. Chem. Teach.* 42 (1968).

Other modifications and alterations of this invention will become apparent to those skilled in the art from the foregoing discussion and accompanying drawing, and it should be understood that this invention is not to be unduly limited thereto.

I claim:

1. The Diels-Alder dimer of N-phenyl-1,3-butadiene-2,3-dicarboximide.

2. The Diels-Alder dimer of N-alkyl-1,3-butadiene-2,3-dicarboximide.

3. The Diels-Alder dimer of N-alkyl-1,3-butadiene-2,3-dicarboximide of claim 2 wherein said alkyl is methyl.

* * * * *